United States Patent
Widdison

(10) Patent No.: US 9,518,017 B2
(45) Date of Patent: Dec. 13, 2016

(54) PURIFICATION OF INTERMEDIATES USED IN THE PREPARATION OF HETEROBIFUNCTIONAL LINKERS

(71) Applicant: ImmunoGen, Inc., Waltham, MA (US)

(72) Inventor: Wayne C. Widdison, Belmont, MA (US)

(73) Assignee: ImmunoGen, Inc., Waltham, MA (US)

( * ) Notice: Subject to any disclaimer, the term of this patent is extended or adjusted under 35 U.S.C. 154(b) by 0 days.

(21) Appl. No.: 14/897,675

(22) PCT Filed: Jun. 26, 2014

(86) PCT No.: PCT/US2014/044268
§ 371 (c)(1),
(2) Date: Dec. 11, 2015

(87) PCT Pub. No.: WO2014/210267
PCT Pub. Date: Dec. 31, 2014

(65) Prior Publication Data
US 2016/0137604 A1   May 19, 2016

Related U.S. Application Data

(60) Provisional application No. 61/840,865, filed on Jun. 28, 2013, provisional application No. 61/840,984, filed on Jun. 28, 2013.

(51) Int. Cl.
*C07D 213/71*   (2006.01)

(52) U.S. Cl.
CPC ................... *C07D 213/71* (2013.01)

(58) Field of Classification Search
CPC .................................. C07D 213/71
See application file for complete search history.

(56) References Cited

U.S. PATENT DOCUMENTS

| 6,441,163 | B1 | 8/2002 | Chari et al. |
| 2004/0039176 | A1 | 2/2004 | Widdison |

OTHER PUBLICATIONS

Tokutake et al., "Bridging group effects on nearest-neighbor recognition within fluid phospholipid membranes," *Langmuir*, 16:81-86 (1999).

Widdison et al., "Semisynthetic Maytansine analogues for the targeted treatment of cancer," *J. Med., Chem.*, 49(14):4392-4408 (2006).

*Primary Examiner* — Noble Jarrell
*Assistant Examiner* — John S Kenyon
(74) *Attorney, Agent, or Firm* — McCarter & English, LLP; Steven G. Davis; Xin Zhang

(57) ABSTRACT

The present invention is directed to a method of separating a monocarboxylic represented by the following structural formula: (I) from a dicarboxylic acid represented by the following structural formula: (II) using silica chromatography.

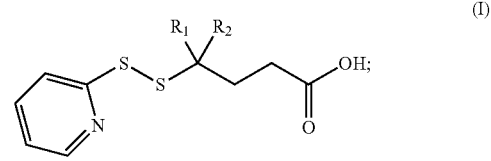

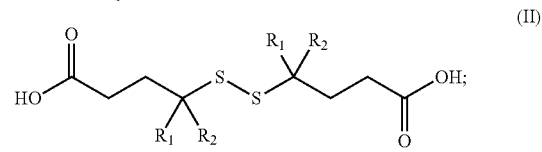

14 Claims, 1 Drawing Sheet

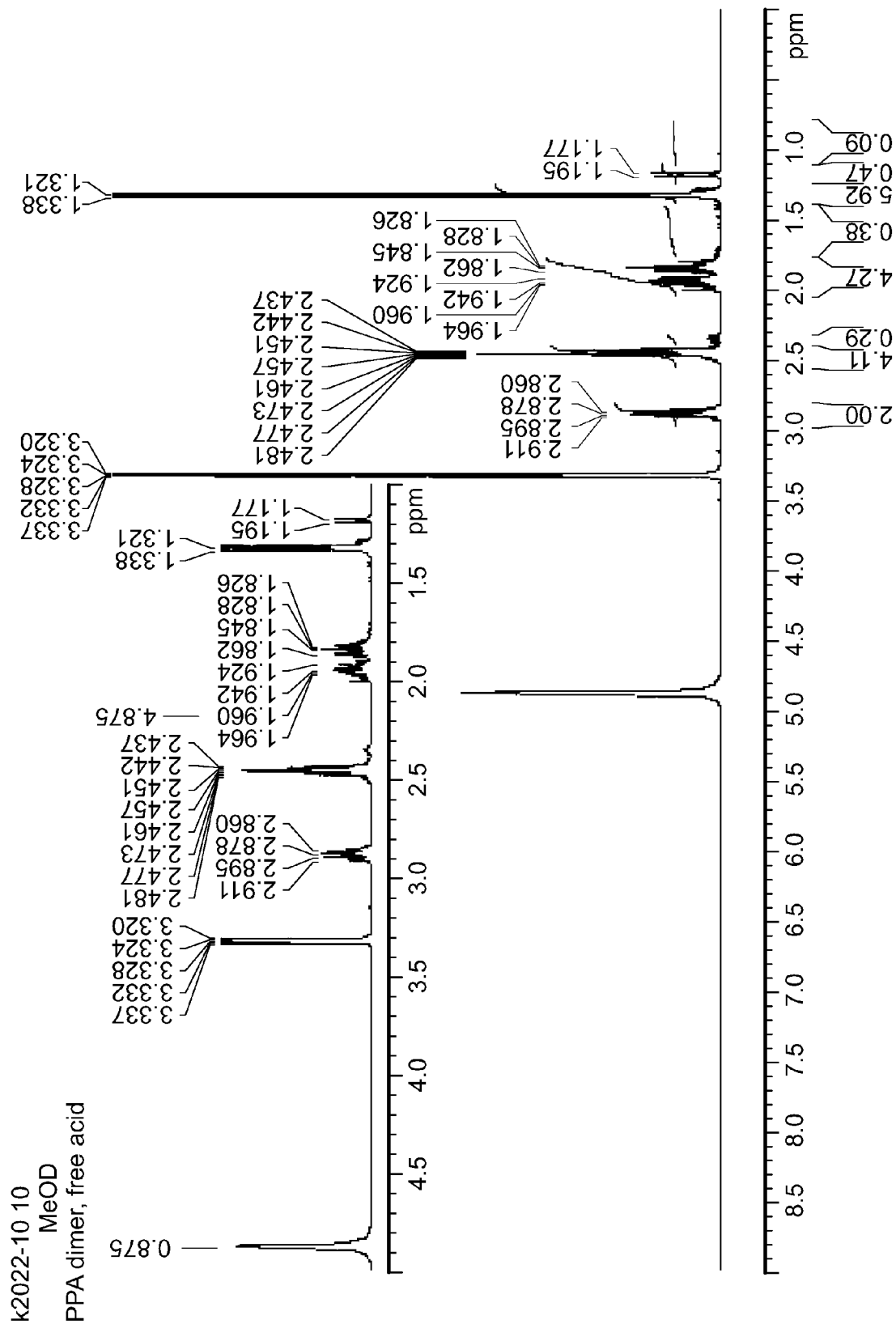

PURIFICATION OF INTERMEDIATES USED IN THE PREPARATION OF HETEROBIFUNCTIONAL LINKERS

REFERENCE TO RELATED APPLICATIONS

This application is a U.S. national stage filing under 35 U.S.C. §371 based on International Application No. PCT/US2014/044268, filed on Jun. 26, 2014, which claims the benefit of the filing date, under 35 U.S.C. §119(e), of U.S. Provisional Application No. 61/840,865 filed on Jun. 28, 2013 and U.S. Provisional Application No. 61/840,984 filed on Jun. 28, 2013, the entire contents of each of which are incorporated herein by reference.

BACKGROUND OF THE INVENTION

Heterobifunctional linkers possessing a reactive ester are useful for conjugating cytotoxic agents to a cell binding agent bearing an amine moiety, such as an antibody. Heterobifunctional linkers such as SPP and SPDB are typically prepared from monocarboxylic acid precursors by

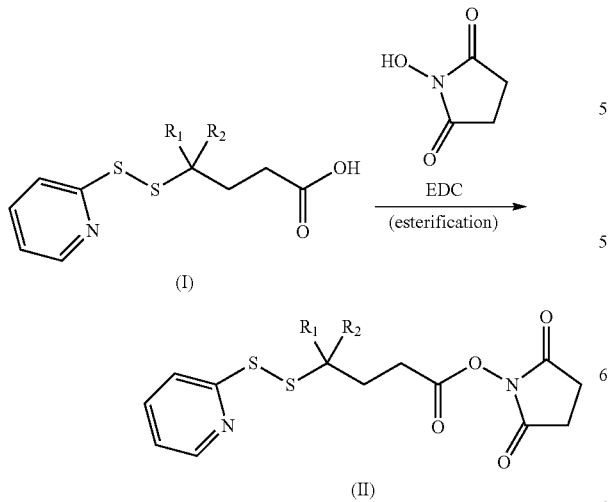

esterification, an example of which is shown below:

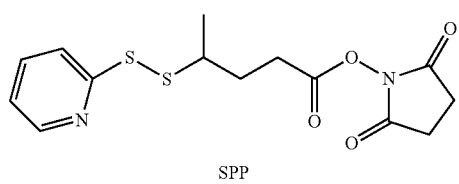

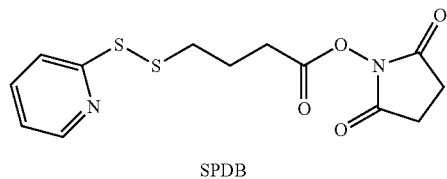

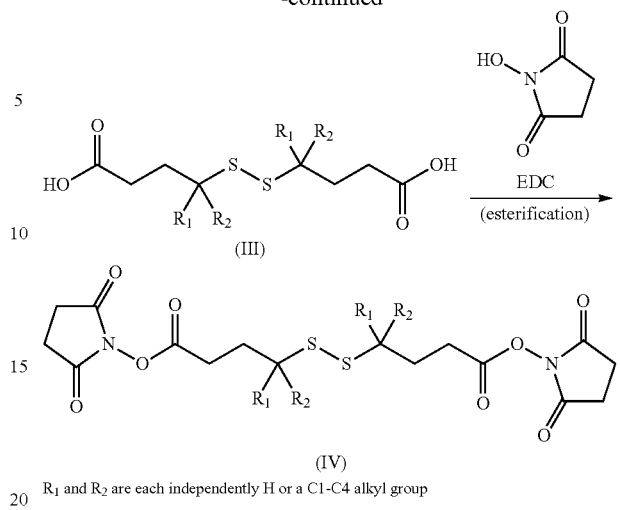

$R_1$ and $R_2$ are each independently H or a C1-C4 alkyl group

If the monocarboxylic acids (I) were contaminated with dicarboxylic acid (III), then undesired homo-bifunctional linker (IV) would also be prepared as an impurity (see the reaction schemes above). It is known that di-carboxylic acid (III) can be generated as an impurity during the reaction of reactive disulfides with thiol-acid precursor (V) (see the reaction scheme below, U.S. Pat. No. 4,149,003). Therefore, purifications methods suitable for large scale commercial use for the separation of the desired monocarboxylic acid (I) from the undesired dicarboxylic acid (III) are needed.

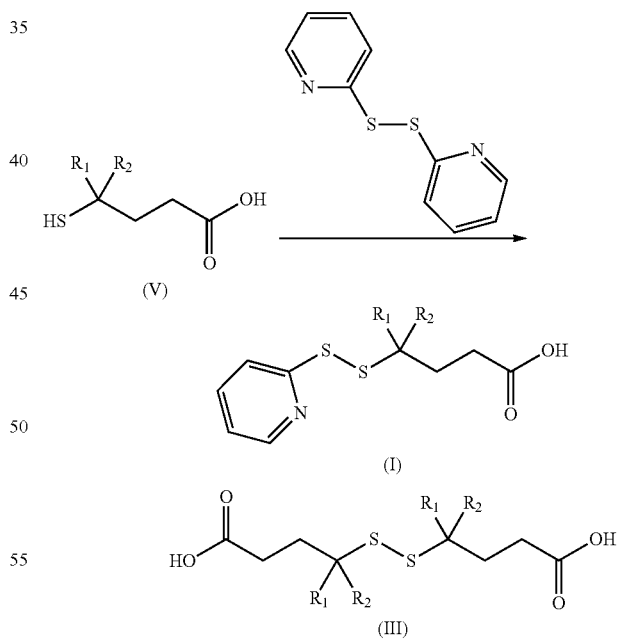

SUMMARY OF THE INVENTION

The invention herein describes a process to more effectively remove dicarboxylic acids (III) from monocarboxylic acids using silica chromatography. Typically, the monocarboxylic acid (I) would be purified by silica chromatography, but removal of the dicarboxylic acid (III) can be difficult. In particular, pyridyldithiocarboxylic acids of this type are often eluted from silica columns using a mobile phase containing acetic acid. It was, however, found that elution of monocarboxylic acid compounds with acetic acid in the mobile phase can also elute dicarboxylic acid impurities so that there is little separation of desired mono-acid from undesired di-acid. A new process has been developed in which crude mono-acid is loaded onto a silica column and then eluted with mobile phase that does not contain acetic acid or any acid component. The new chromatography results in an improved separation of dicarboxylic acid species from the desired monocarboxylic acid.

BRIEF DESCRIPTION OF THE FIGURES

FIG. 1 is the $^1$H NMR of the undesired dicarboxylic dimer isolated from PPA.

DETAILED DESCRIPTION OF CERTAIN EMBODIMENTS

The present invention is directed to a method of separating a monocarboxylic acid represented by the following structural formula:

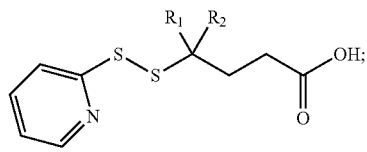

from a dicarboxylic acid represented by the following structural formula:

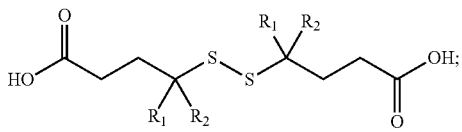

in a mixture comprising the mono and dicarboxylic acids, wherein $R_1$ and $R_2$ are each independently H or a C1-C4 alkyl group, said method comprising the steps of:
1) applying the mixture to a silica gel column; and
2) separating the monocarboxylic acid and the dicarboxylic acid by eluting them from the silica gel column using an elution solvent system and collecting an eluent comprising the monocarboxylic acid,
wherein the elution solvent system comprises an organic solvent in the absence of an acid.

In one embodiment, the eluent comprising the monocarboxylic acid is free of the dicarboxylic acid. Alternatively, the eluent comprises the monocarboxylic acid and the dicarboxylic acid, wherein the dicarboxylic acid is less than 5%, 4%, 3%, 2%, 1%, 0.5%, 0.4%, 0.3%, 0.2%, or 0.1% of the combined weight of the monocarboxylic acid and the dicarboxylic acid.

In one embodiment, the eluent is collected in fractions and the fraction size is adjusted to separate the monocarboxylic acid and the dicarboxylic acid in separate fractions. The fraction size can be readily determined by a skilled person in the art, depending partly on the difference in elution time between the monocarboxylic acid and the dicarboxylic acid, the amount of the crude product containing the monocarboxylic acid and dicarboxylic acid to be separated, etc.

In another embodiment, the elution solvent system comprises a non-polar organic solvent and a polar organic in the absence of an acid. The acid can be an organic acid or an inorganic acid. In one embodiment, the elution solvent system is absent of acetic acid.

Any polar organic solvent known in the art can be used. Polar solvents are solvents with high dielectric points, for example greater than 15. For example, polar solvents are those high strength solvents described in *The HPLC Solvent Guide* (2$^{nd}$ Edition by Paul Sadek, 2002, John Wiley and Sons, New York, N.Y., ISBN-13 978-0471411383). In one embodiment, a polar solvent is an ester solvent, ether or an alcohol solvent. Polar solvent can be selected from the group consisting of is methyl acetate, ethyl acetate, ethyl formate, methyl propionate, ethyl propionate, propyl propionate, tetrahydrafuran, 2-methyl tetrahydrofuran, methanol, ethanol, propanol, dimethoxyethane or a mixture of any of the foregoing. Any non-polar solvents known in the art can be used in the present invention. Exemplary non-polar solvents include halogenated solvents such as carbon tetrachloride, chloroform, or hydrocarbon solvents, such as, but not limited to, pentane, hexane, hexanes, heptane, octane, petroleum ether, benzene, toluene or a mixture of any of the forgoing. In one embodiment, the elution solvent system is a mixture of heptane and ethyl acetate.

The volume ratio of the non-polar organic solvent (e.g., hydrocarbon solvent, such as heptane) and the polar organic solvent (e.g., ethyl acetate) can be adjusted to optimize the separation of the monocarboxylic acid and the dicarboxylic acid. In one embodiment, the volume ratio of the hydrocarbon solvent to the polar organic solvent can be between about 1:1 and about 10:1, between about 2:1 and about 6:1, between about 3:1 and about 5:1, between about 3.5:1 and about 4.5:1 or between about 3.9:1 and 4.1:1. In one embodiment, the volume ratio of the hydrocarbon solvent to the polar organic solvent is about 4:1.

In one embodiment, the mobile phase (i.e., elution solvent system) is kept constant during the elution, known as isocratic elution mode. Alternatively, the mobile phase (i.e., elution solvent system) is varied during elution, known as gradient elution mode. In gradient elution, the elution solvent system can be varied from low polarity to high polarity. The increase in polarity can be achieved by decreasing the volume ratio of the non-polar organic solvent to the polar organic solvent. Alternatively, the elution solvent system can be varied from high polarity to low polarity. In another alternative, a gradient elution can be followed by an isocratic elution, or vice versa.

The amount of the silica gel needed to separate the monocarboxylic acid and the dicarboxylic acid can be readily determined by one of ordinary skill in the art, depending on the elution solvent system used, the amount of the crude product containing monocarboxylic acid and dicarboxylic acid, etc.

The disclosed methods provide highly pure monocarboxylic acid (I) that is substantially free of the dicarboxylic acid (III). For example, the monocarboxylic acid (I) is greater than 95%, 96%, 97%, 98%, 99%, 99.5%, 99.6%, 99.7%, 99.8%, or 99.9% pure by weight. Alternatively, the monocarboxylic acid (I) is between 95-99.9%, 96-99.9%, 97-99.9%, 98-99.9%, 99-99.9%, 99.5-99.9%, 99.6-99.9%, 99.7-99.9% or 99.8-99.9% pure by weight. In another alternative, the monocarboxylic acid (I) is between 95-99%, 96-99%, 97-99% or 98-99% pure by weight.

In another embodiment, the invention is a composition comprising monocarboxylic acid (I) and optionally dicarboxylic acid (III), wherein the dicarboxylic acid (III) is less than 5%, 4%, 3%, 2%, 1%, 0.5%, 0.4%, 0.3%, 0.2% or 0.1% of the combined weight of the monocarboxylic acid (I) and dicarboxylic acid (III) in the composition. Specifically, the dicarboxylic acid (III) is less than 0.1% of the combined weight of the monocarboxylic acid (I) and dicarboxylic acid (III) in the composition or the composition is free of the dicarboxylic acid (III).

In another embodiment, the purified monocarboxylic acid described herein can be converted to a reactive ester derivative (II'):

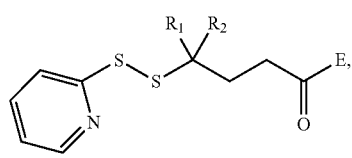

wherein the group —C(=O)E represents a reactive ester or thioester group and the reminder of the variables is defined as in formula (I). In one embodiment, the reactive ester or thioester group is an N-hydroxysuccinimide ester, N-hydroxy sulfosuccinimide ester, nitrophenyl ester, dinitrophenyl ester, tetrafluoro phenyl ester, pentafluorophenyl ester, a thiopyridyl ester, or a thionitrophenyl ester. Specifically, the reactive ester group is an N-hydroxysuccinimide ester. In one embodiment, the reactive ester derivative (II') is represented by formula (II):

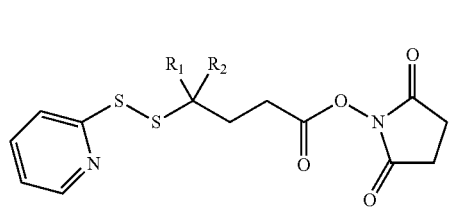

The reactive ester derivative (II') can be obtained by reacting the monocarboxylic acid (I) with a hydroxy or mercapto compound in the presence of a coupling reagent. Specifically, the hydroxy or mercapto compound is selected from, but not limited to, N-hydroxysuccinimide, N-hydroxy sulfo-succinimide, tetrafluorophenol, pentafluorophenol, nitrophenol, dinitrophenol, thiopyridine or nitrobenzenethiol. More specifically, the hydroxy or mercapto compound is N-hydroxysuccinimide. Specifically, the coupling agent is selected from, but not limited to N,N'-dicyclohexylcarbodiimide (DCC), 1-ethyl-3-(3-dimethylaminopropyl) carbodiimide (EDC), N,N'-diisopropyl carbodiimide (DIC), 1-ethoxycarbonyl-2-ethoxy-1,2-dihydroquinoline (EEDQ). More specifically, the coupling agent is EDC. Optionally, an additional reagent such as HATA, HBTU, DMAP can be added to speed up the reaction.

In another embodiment, the purified monocarboxylic acid described herein can be converted to a reactive ester derivative (VI'):

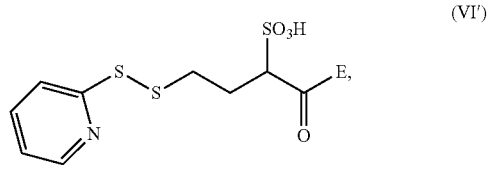

wherein the group —C(=O)E represents a reactive ester or thioester group. In one embodiment, the reactive ester or thioester group is an N-hydroxysuccinimide ester, N-hydroxy sulfosuccinimide ester, nitrophenyl ester, dinitrophenyl ester, tetrafluoro phenyl ester, pentafluorophenyl ester, a thiopyridyl ester, or a thionitrophenyl ester. Specifically, the reactive ester group is an N-hydroxysuccinimide ester. In one embodiment, the reactive ester derivative (VI') is represented by formula (VI):

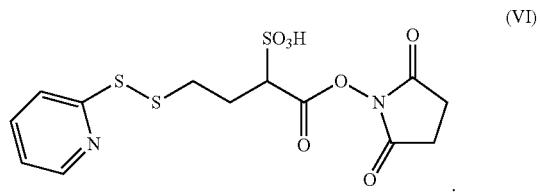 [SMILES: O=C(ON1C(=O)CCC1=O)C(CCSSc1ccccn1)S(=O)(=O)O]

The reactive ester derivative (VI') can be obtained by reacting the monocarboxylic acid (I) with a sulfonating agent optionally in the presence of a base to provide the compound of formula (VII) (e.g., see US 2012/0165537, incorporated herein by reference), followed by reacting the compound of formula (VII) with a hydroxy or mercapto compound in the presence of a coupling reagent.

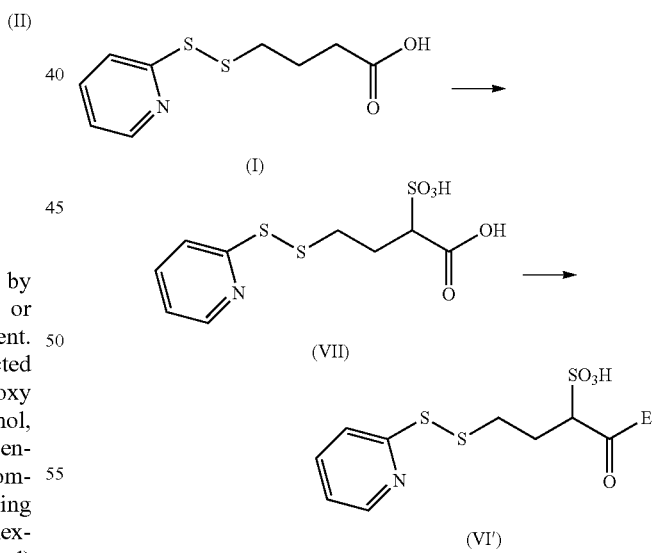

Specifically, the sulfonating agent is selected from, but not limited to, chlorosulfonic acid and sulfur trioxide. More specifically, the sulfonating agent is chlorosulfonic acid. Specifically, the base is selected from, but not limited to, trialkylamine, such as triethyl amine, diisopropylethyl amine (DIPEA) or tributyl amine, or 4-alkylmorpholine, such as 4-methylmorpholine. More specifically, the base is diisopropylethyl amine;

Specifically, the hydroxy or mercapto compound is selected from, but not limited to, N-hydroxysuccinimide, N-hydroxy sulfo-succinimide, tetrafluorophenol, pentafluorophenol, nitrophenol, dinitrophenol, thiopyridine or nitrobenzenethiol. More specifically, the hydroxy or mercapto compound is N-hydroxysuccinimide. Specifically, the coupling agent is selected from, but not limited to N,N'-dicyclohexylcarbodiimide (DCC), 1-ethyl-3-(3-dimethylaminopropyl)carbodiimide (EDC), N,N'-diisopropyl carbodiimide (DIC), 1-ethoxycarbonyl-2-ethoxy-1,2-dihydroquinoline (EEDQ). More specifically, the coupling agent is EDC. Optionally, an additional reagent such as HATA, HBTU, DMAP can be added to speed up the reaction.

The reactive ester derivative (II'), (II), (VI') or (VI) is useful for conjugating cytotoxic agents to a cell-binding agent bearing an amine moiety, such as an antibody. In one embodiment, the cytotoxic agent is a maytansinoid, specifically N2'-deacetyl-N2'-(3-mercapto-1-oxopropyl)-maytansine (DM1) or N2'-deacetyl-N2'-(4-methyl-4-mercapto-1-oxopentyl)-maytansine (DM4).

In one embodiment, for compounds of formulae (I), (II), (II'), (III), (IV) or (V), $R_1$ and $R_2$ are both H. Alternatively, $R_1$ is H and $R_2$ is methyl.

"C1-C4 alkyl" as used herein refers to a saturated linear or branched-chain monovalent hydrocarbon radical having one to four carbon atoms. Examples of C1-C4 alkyl include methyl, ethyl, 1-propyl, 2-propyl, 1-butyl, 2-methyl-1-propyl, 2-butyl and 2-methyl-2-propyl. Specifically, C1-C4 alkyl is methyl or ethyl.

EXEMPLIFICATION

Example 1

Reaction of 4-Mercapto-Pentanoic Acid with 2,2'-Dithiopyridine

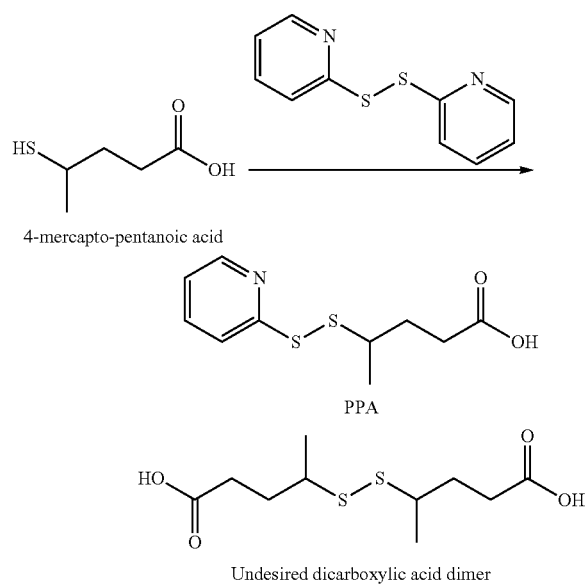

2,2'-dithiodipyridine (Aldrithiol, 100 g, 454 mmol) was dissolved in ethanol (700 mL) to which acetic acid (280 mL) was added and the solution was magnetically stirred in an ice/water bath until it reached 14.9° C. A solution of 4-mercapto-pentanoic acid (30 g, 220 mmol) in ethyl acetate (140 mL) was then added over 15 min with stirring. After addition the cooling bath was removed and the reaction was stirred for 2 h and 25 min. Solvent was evaporated under vacuum to give a yellow gum residue.

Example 2

Unsuccessful Separation of PPA from the Undesired Dicarboxylic Acid Dimer in the Presence of Acetic Acid The residue from Example 1 was taken up in dichloromethane (60 mL). A dry packed silica column (1.46 Kg silica, 60 A pore size, 230-400 mesh) was equilibrated with 4:1 heptane:ethyl acetate (3.4 L). The residue in dichloromethane was then loaded on the column and the column was eluted with 4:1 heptane:ethyl acetate 7.8 L to elute off the unreacted 2,2'-dithiodipyridine then the column was eluted with (4:1 heptane:ethyl acetate containing 2% acetic acid) collecting 13 fractions with volumes between 200 mL-250 mL. The fractions were analyzed by silica TLC and each of the 11 fractions containing desired product (PPA) were contaminated with varying levels of PPA dimer impurity. Fractions containing less than 0.5% of the impurity by HPLC area 252 nm were combined and solvent was removed under vacuum to give 29.2 g (41% yield) of desired product which contained 0.4% PPA dimer. A repeat of this experiment again gave desired product that was contaminated with undesired PPA dimer.

A fraction containing a larger amount of the dicarboxylic acid dimer component was evaporated to dryness and taken up in a minimum volume of DMSO then purified by reverse phase HPLC preparative method 1. Fractions containing the dicarboxyic acid dimer were combined in a 100 mL flask and the flask was placed in a dry ice/acetone bath to freeze the contents then the sample was lyophilized. Deuterated chloroform (5 mL) was added to the flask and swirled then evaporated. Deuterated methanol was added and the solution was analyzed by $^1$H NMR (shown in the Figure), which confirmed the compound was the dicarboxylic acid dimer.

HPLC Preparative Method 1
Column: Kromasil C18 250 x
Solvent A: Deionized water containing 0.2% formic acid
Solvent B: Acetonitrile
Detection: 220-252 nm
Injection volume: 200 µL per run
Gradient:
Time % B
  0 5
  30 95

Example 3

Successful Separation of PPA from the Undesired Dicarboxylic Acid Dimer Without Acetic Acid in the Silica Gel Column Mobile Phase 2,2'-dithiodipyridine (Aldrithiol, 100 g, 454 mmol) was dissolved in ethanol (700 mL) to which acetic acid (280 mL) was added and the solution was magnetically stirred in an ice/water bath until it reached 14.9° C. A solution of 4-mercapto-pentanoic acid (30 g, 220 mmol) in ethyl acetate (140 mL) was then added over 15 min with stirring. After addition the cooling bath was removed and the reaction was stirred for 2 h and 25 min. Solvent was evaporated under vacuum to give a yellow gum residue. The residue was taken up in dichloromethane (60 mL). A dry packed silica column (1.46 Kg silica, 60 A pore size, 230-400 mesh) was equilibrated with 4:1 heptane:ethyl acetate (3.4 L). The residue in dichloromethane was then loaded on the column and the column was eluted with 4:1 heptane:ethyl acetate. Unreacted 2,2'-dithiodipyridine eluted first followed by desired PPA. Fractions containing PPA were combined and solvent was removed under vacuum to give 43 g (60.3% yield) of desired product which had no detectable the dicarboxylic dimer. A repeat of this experiment again gave desired product that was not contaminated with undesired dicarboxylic acid dimer.

What is claimed is:

1. A method of separating a monocarboxylic acid represented by the following structural formula:

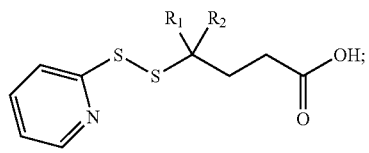

from a dicarboxylic acid represented by the following structural formula:

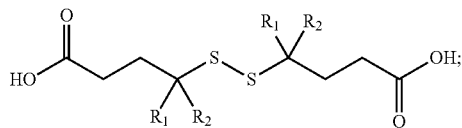

in a mixture comprising the mono and dicarboxylic acids, wherein $R_1$ and $R_2$ are each independently H or a $C_1$-$C_4$ alkyl group, said method comprising the steps of:
1) applying the mixture to a silica gel column; and
2) separating the monocarboxylic acid and the dicarboxylic acid by eluting them from the silica gel column using an elution solvent system and collecting an eluent comprising the monocarboxylic acid, wherein the elution solvent system comprises an organic solvent in the absence of an acid.

2. The method of claim 1, wherein the elution solvent system comprises a non-polar organic solvent and a polar organic solvent in the absence of an organic acid.

3. The method of claim 2, wherein the mixture is the isolated reaction product between a first starting material represented by

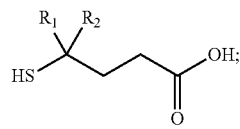

and a second starting material represented by

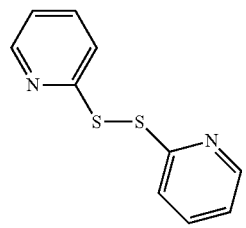

4. The method of claim 2, wherein the polar organic solvent is an organic solvent having a dielectric point of greater than 15.

5. The method of claim 2, wherein the polar organic solvent is an ester solvent.

6. The method of claim 2, wherein the polar organic solvent is an alcohol solvent or an ether solvent.

7. The method of claim 2, wherein the polar organic solvent is methyl acetate, ethyl acetate, ethyl formate, methyl propionate, ethyl propionate, propyl propionate, tetrahydrafuran, 2-methyl tetrahydrofuran, methanol, ethanol, propanol, dimethoxyethane or a mixture of any of the foregoing.

8. The method of claim 7, wherein the non-polar organic solvent is a hydrocarbon solvent.

9. The method of claim 8, wherein the hydrocarbon solvent is pentane, hexane, heptane, octane, petroleum ether or a mixture of any of the forgoing.

10. The method of claim 2 wherein the elution solvent system is a mixture of heptane and ethyl acetate.

11. The method of claim 2, wherein the volume ratio of the non-polar organic solvent to the polar organic solvent is between 1:1 and 10:1.

12. The method of claim 11, the volume ratio of the non-polar organic solvent to the polar organic solvent is 4:1.

13. The method of claim 1, wherein $R_1$ and $R_2$ are both hydrogen.

14. The method of claim 1, wherein $R_1$ is hydrogen and $R_2$ is methyl.

* * * * *